(12) United States Patent
Shenai-Khatkhate et al.

(10) Patent No.: US 7,767,840 B2
(45) Date of Patent: Aug. 3, 2010

(54) ORGANOMETALLIC COMPOUNDS

(75) Inventors: Deodatta Vinayak Shenai-Khatkhate, Danvers, MA (US); Michael Brendan Power, Newburyport, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 28 days.

(21) Appl. No.: 12/228,346

(22) Filed: Aug. 12, 2008

(65) Prior Publication Data

US 2009/0156852 A1 Jun. 18, 2009

Related U.S. Application Data

(62) Division of application No. 10/817,618, filed on Apr. 2, 2004, now Pat. No. 7,413,776.

(60) Provisional application No. 60/460,791, filed on Apr. 5, 2003, provisional application No. 60/513,476, filed on Oct. 22, 2003.

(51) Int. Cl.
C07F 7/30 (2006.01)
(52) U.S. Cl. .................. 556/87; 556/81; 556/95; 556/104
(58) Field of Classification Search .................. 556/81, 556/87, 95, 104
See application file for complete search history.

(56) References Cited

U.S. PATENT DOCUMENTS

| | | |
|---|---|---|
| 2,444,270 A | 6/1948 | Rochow |
| 3,442,921 A | 5/1969 | Grant et al. |
| 3,446,824 A | 5/1969 | Moedritzer |
| 3,470,220 A | 9/1969 | Moedritzer et al. |
| 3,935,040 A | 1/1976 | Mason |
| 3,985,590 A | 10/1976 | Mason |
| 4,506,815 A | 3/1985 | Melas et al. |
| 4,720,561 A | 1/1988 | Bradley et al. |
| 4,812,586 A | 3/1989 | Mullin et al. |
| 4,877,651 A | 10/1989 | Dory |
| 5,120,394 A | 6/1992 | Mukai |
| 5,316,958 A | 5/1994 | Meyerson |
| 5,459,108 A | 10/1995 | Doi et al. |
| 5,489,550 A | 2/1996 | Moslehi |
| 5,502,227 A | 3/1996 | Kanjolia et al. |
| 5,593,741 A | 1/1997 | Ikeda |
| 5,755,885 A | 5/1998 | Mikoshiba et al. |
| 5,874,368 A | 2/1999 | Laxman et al. |
| 5,976,991 A | 11/1999 | Laxman et al. |
| 6,099,903 A | 8/2000 | Kaloyeros et al. |
| 6,126,996 A | 10/2000 | Kirlin et al. |
| 6,159,855 A | 12/2000 | Vaartstra |
| 6,214,729 B1 | 4/2001 | Uhlenbrock et al. |
| 6,238,734 B1 | 5/2001 | Senzaki et al. |
| 6,306,217 B1 | 10/2001 | Uhlenbrock et al. |
| 6,310,228 B1 | 10/2001 | Itsuki et al. |
| 6,359,159 B1 | 3/2002 | Welch et al. |
| 6,391,803 B1 | 5/2002 | Kim et al. |
| 6,444,038 B1 | 9/2002 | Rangarajan et al. |
| 6,444,041 B2 | 9/2002 | Vaarststra |
| 6,444,818 B2 | 9/2002 | Uhlenbrock et al. |
| 6,492,711 B1 | 12/2002 | Takagi et al. |
| 6,509,587 B2 | 1/2003 | Sugiyama et al. |
| 6,514,886 B1 | 2/2003 | U'Ren |
| 6,589,329 B1 | 7/2003 | Baum et al. |
| 6,642,401 B2 | 11/2003 | Watanabe et al. |
| 6,869,638 B2 | 3/2005 | Baum et al. |
| 7,005,392 B2 | 2/2006 | Baum et al. |
| 7,045,451 B2 | 5/2006 | Shenai-Khatkhate |
| 2001/0000476 A1 | 4/2001 | Xia et al. |
| 2001/0048973 A1 | 12/2001 | Sato et al. |
| 2002/0090835 A1 | 7/2002 | Chakravarti et al. |
| 2002/0180028 A1 | 12/2002 | Borovik et al. |
| 2003/0082300 A1 | 5/2003 | Todd et al. |
| 2003/0111013 A1 | 6/2003 | Oosterlaken et al. |
| 2003/0230233 A1 | 12/2003 | Fitzgerald et al. |
| 2004/0259333 A1 | 12/2004 | Tomasini et al. |
| 2006/0172068 A1 | 8/2006 | Ovshinsky |

FOREIGN PATENT DOCUMENTS

| | | |
|---|---|---|
| EP | 0 481 706 | 4/1994 |
| EP | 0 368 651 | 9/1994 |
| EP | 1 160 355 A2 | 12/2001 |
| FR | 2 722 781 | 1/1996 |
| GB | 626 398 | 4/1946 |
| GB | 1 386 900 | 3/1975 |
| WO | WO 2004/011473 A1 | 2/2004 |

OTHER PUBLICATIONS

Satge et al., Helvetica Chimica Acta, vol. 55, No. 7, pp. 2406-2418 (1972).*
Dittmar et al., "Cyclopentadienyl Germanes as Novel Precursors for the CVD of Thin Germanium Films", Chem. Vap. Deposition 2001, 7, No. 5, pp. 193-195.
Harrison et al., "Predeposition Chemistry Underlying the Formation of Germanium Films by CVD of Tetravinylgermane", Chem. Mater. 1994, 6, pp. 1620-1626.
Hoffman et al., "Plasma-enhanced chemical vapor deposition of silicon, germanium, and tin nitride thin films from metalorganic precursors", J. Vac. Sci. Technol. A 13(3), May/Jun. 1995, pp. 820-825.
O. Johnson, "The Germanes and Their Organo Derivatives", Chem. Rev. 1951, 48, 259, pp. 259-297.
Kidd et al., "Germanium-73 Nuclear Magnetic Resonance Spectra of Germanium Tetrahalides", Journal of American Chemical Society, 95:1, Jan. 10, 1973, pp. 88-90.

(Continued)

Primary Examiner—Porfirio Nazario Gonzalez
(74) Attorney, Agent, or Firm—S. Matthew Cairns

(57) ABSTRACT

Organometallic compounds suitable for use as vapor phase deposition precursors for Group IV metal-containing films are provided. Methods of depositing Group IV metal-containing films using certain organometallic precursors are also provided. Such Group IV metal-containing films are particularly useful in the manufacture of electronic devices.

5 Claims, No Drawings

OTHER PUBLICATIONS

H. Ohshima, "Organo-germanium adsorption on a silicon surface by excimer light irradiation", Applied Surface Science 107 (1996), pp. 85-89.

Bottei et al., "Organogermanium Chemistry", Chem. Rev. (1951), 48, 259, pp. 403-442.

Sulkes et al., "Molecular beam study of possible CVD intermediates from Group-14 organometallic precursors", Chemical Physics Letters 318 (2000), pp. 448-453.

D. Smith, Structural Properties of heteroepitaxial germanium-carbon alloys grown in Si(100); Philosophical Magazine A, 2001, vol. 81, No. 6, pp. 1613-1624.

Todd et al., "Influence on Precursor Chemistry on Synthesis of Silicon-Carbon Germanium Alloys", Mat. Res. Soc. Symp. Proc. vol. 377, 1955, pp. 529-534.

Dillon et al., "Comparison of Trichlorosilane and Trichlorogermane Decomposition on Silicon Surfaces Using FTIR Spectroscopy", Mat. Res. Soc. Symp. Proc. vol. 282, 1993, pp. 405-411.

Dillon et al., "Adsorption and Decomposition of Diethylgermane on porous silicon surfaces", Surface Science Letters 286 (1993), pp. L535-L541.

Todd et al., Chemical Synthesis of Metastable Geramanium-Carbon Alloys Grown Heteroepitaxially on (100) Si: Chem. Mater. 1996, 8 pp. 2491-2498.

Coon et al., "Germanium Deposition on Silicon: Surface Chemistry of $(CH_3CH_2)_2GeH_2$ and $GeCl_4$", Mat. Res. Soc. Symp. Proc. vol. 282, 1993, pp. 413-419.

Kouvetakis et al., "Novel Chemical Routes to Silicon-Germanium-Carbon Materials", Appl. Phys. Lett. 65(23); Dec. 5, 1994, pp. 2960-2962.

Dillon et al., "Adsorption and Decomposition of Trichlorosilane and Trichlorogermane on Porous Silicon and Si(100) 2×1 Surfaces", J. Vac. Sci. Technol. A 13(1); Jan./Feb. 1995; pp. 1-10.

Beckler et al., "Highly Conformal Thin Films of Tungsten Nitride Prepared by Atomic Layer Deposition from a Novel Precursor", Chem. Mater., 15 (15), 2003, pp. 2969-2976.

Son et al., "Growth Rate and Microstructure of Copper Thin Films . . . " Thin Solid Films 335 (1998), pp. 229-236.

European Search Report of corresponding European Patent Application No. EP 08 16 3178.

Pola et al.; "Chemical Vapour Deposition of Germanium Films by Laser-Induced Photolysis of Ethygermanes"; Journal of the Chemical Society—Faraday Transactions; vol. 88, No. 12, Jun. 21, 1992; pp. 1637-1641.

Mazerolles et al.; "Precurseurs organometalliques de couches minces amorphes semiconductrices—I. Thermolyse de derives organogermanes beta-ethyleniques (phase gazeuse)"; Journal of Organometallic Chemistry, vol. 328, No. 1-2, Jul. 14, 1987; pp. 49-59.

* cited by examiner

ORGANOMETALLIC COMPOUNDS

This application is a divisional of Ser. No. 10/817,618, filed on Apr. 2, 2004 now U.S. Pat. No. 7,413,776, which patent claims the benefit of provisional application Ser. No. 60/460,791, filed on Apr. 5, 2003 and provisional application Ser. No. 60/513,476, filed on Oct. 22, 2003.

BACKGROUND OF THE INVENTION

The present invention relates generally to the field of organometallic compounds. In particular, the present invention relates to the certain organometallic compounds suitable for use in vapor deposition processes.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). Chemical vapor deposition processes, such as metalorganic chemical vapor deposition ("MOCVD"), deposit a metal layer by decomposing organometallic precursor compounds at elevated temperatures, i.e., above room temperature, either atmospheric pressure or at reduced pressures. A wide variety of metals may be deposited using such CVD or MOCVD processes.

For semiconductor and electronic device applications, these organometallic precursor compounds must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

For certain applications where high speed and frequency response of an electronic device is desired, silicon-only devices, e.g. silicon bipolar transistors, have not been competitive. In a heterojunction bipolar transistor ("HBT"), a thin silicon-germanium layer is grown as the base of a bipolar transistor on a silicon wafer. The silicon-germanium HBT has significant advantages in speed, frequency response, and gain when compared to a conventional silicon bipolar transistor. The speed and frequency response of a silicon-germanium HBT are comparable to more expensive gallium-arsenide HBTs.

The higher gain, speeds, and frequency response of silicon-germanium HBTs have been achieved as a result of certain advantages of silicon-germanium not available with pure silicon, for example, narrower band gap and reduced resistivity. Silicon-germanium may be epitaxially grown on a silicon substrate using conventional silicon processing and tools. This technique allows one to engineer device properties such as the energy band structure and carrier mobility. For example, it is known in the art that grading the concentration of germanium in the silicon-germanium base builds into the HBT device an electric field or potential gradient, which accelerates the carriers across the base, thereby increasing the speed of the HBT device compared to a silicon-only device. A common method for fabricating silicon and silicon-germanium devices is by CVD. A reduced pressure chemical vapor deposition technique ("RPCVD") used to fabricate the HBT device allows for a controlled grading of germanium concentration across the base layer as well as precise control over the doping profile.

Germane ($GeH_4$) is the conventional precursor for germanium deposition while silane ($SiH_4$), and dichlorosilane ($SiH_2Cl_2$) are conventional precursors for silicon deposition. These precursors are difficult to handle and have high vapor pressures. For example, germane decomposes violently at 280° C., which is below the temperature used to grow germanium films. Accordingly, processes employing either germane or silane require extensive safety procedures and equipment. Germane typically requires film growth temperatures of approximately 500° C. or higher for thermal CVD applications. Such decomposition temperatures are not always suitable, such as in mass production applications where there is a need for lower temperatures, e.g. 200° C. Other CVD applications require higher growth temperatures which cause conventional precursors to break up prematurely which, in turn, leads to the formation of particles and a reduction in metal film growth rates. A further problem with conventional silicon and germanium precursors is that when a relatively stable silicon precursor and a relatively unstable germanium precursor are used to deposit a silicon-germanium film, the differences in precursor stability makes control of the silicon-germanium composition difficult. There is a need for precursors for silicon and germanium vapor phase deposition that are safer to handle and have decomposition temperatures tailored to specific conditions. There is also a desire for silicon and germanium precursors that have matched stability characteristics.

SUMMARY OF THE INVENTION

The present inventors have surprisingly found that the above deficiencies can be remedied. The present invention provides a method of depositing a metal-containing film on a substrate including the steps of: a) conveying one or more of the organometallic compounds of formula I in a gaseous phase to a deposition chamber containing the substrate,

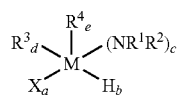

(I)

wherein M is Si or Ge; $R^1$ and $R^2$ are independently chosen from H, alkyl, alkenyl, alkynyl and aryl; each $R^3$ is independently chosen from ($C_1$-$C_{12}$)alkyl, alkenyl, alkynyl and aryl, provided that $R^3$ is not cyclopentadienyl; each $R^4$ is independently chosen from ($C_3$-$C_{12}$)alkyl; X is halogen; a=0-3; b=0-3; c=0-3; d=0-3; e=0-4; and a+b+c+d+e=4; wherein $R^3 \neq R^4$; wherein the sums of a+b and a+d are each $\leq 3$; provided that when M=Si the sum of b+c is $\leq 3$; b) decomposing the one or more organometallic compounds in the deposition chamber; and c) depositing the metal film on the substrate.

Also, the present invention provides a device for feeding a fluid stream saturated with an organometallic compound suitable for depositing a metal film containing silicon, germanium and combinations thereof to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing one or more organometallic compounds of formula I

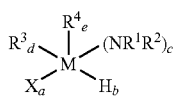

(I)

wherein M is Si or Ge; $R^1$ and $R^2$ are independently chosen from H, alkyl, alkenyl, alkynyl and aryl; each $R^3$ is independently chosen from $(C_1-C_{12})$alkyl, alkenyl, alkynyl and aryl, provided that $R^3$ is not cyclopentadienyl; each $R^4$ is independently chosen from $(C_3-C_{12})$alkyl; X is halogen; a=0-3; b=0-3; c=0-3; d=0-3; e=0-4; and a+b+c+d+e=4; wherein $R^3 \neq R^4$; wherein the sums of a+b and a+d are each $\leq 3$; provided that when M=Si the sum of b+c is $\leq 3$; the inlet opening being in fluid communication with the chamber and the chamber being in fluid communication with the outlet opening.

Another embodiment of the present invention is an apparatus for vapor deposition of metal films including one or more devices for feeding a fluid stream including one or more organometallic compounds described above.

The present invention further provides an organogermanium compound of formula IIA or IIB:

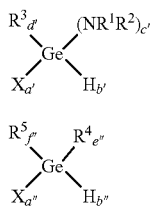

wherein $R^1$ and $R^2$ are independently chosen from alkyl, alkenyl, alkynyl or aryl; each $R^3$ is independently chosen from $(C_1-C_{12})$alkyl, alkenyl, alkynyl and aryl; each $R^4$ is independently chosen from branched and cyclic $(C_3-C_5)$ alkyl; each $R^5$ is independently chosen from $(C_1-C_{12})$alkyl, alkenyl, alkynyl and aryl; X is halogen; a'=0-3; b'=0-2; c'=1-3; d'=0-3; a'+b'+c'+d'=4; a"=0-2; b"=0-2; e"=1-2; f"=0-2; a"+b"+e"+f"=4; wherein at least two of a", b" and f"$\neq$0; provided when a"=1, e"=1, f"=2, and $R^4=(CH_3)C$ that $R^5 \neq CH_3$; and provided that $R^3$ is branched or cyclic $(C_3-C_8)$ alkyl when c'+d'=4.

In further embodiment, the present invention provides a method of depositing a germanium-containing film on a substrate comprising the steps of: a) conveying one or more of the organogermanium compounds described above in a gaseous phase to a deposition chamber containing the substrate; b) decomposing the one or more organogermanium compounds in the deposition chamber; and c) depositing the germanium-containing film on the substrate.

Further, the present invention provides a method of manufacturing an electronic device including the step of depositing a germanium-containing film on a substrate wherein the film is deposited by the steps of: a) conveying one or more of the organogermanium compounds described above in a gaseous phase to a deposition chamber containing the substrate; b) decomposing the one or more organogermanium compounds in the deposition chamber; and c) depositing the germanium-containing film on the substrate.

DETAILED DESCRIPTION OF THE INVENTION

As used throughout this specification, the following abbreviations shall have the following meanings, unless the context clearly indicates otherwise: ° C.=degrees centigrade; NMR=nuclear magnetic resonance; mol=moles; b.p.=boiling point, g=gram; L=liter; M=molar; ca.=approximately; µm=micron=micrometer; cm=centimeter; ppm=parts per million; and mL=milliliter.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The term "SiGe" refers to silicon-germanium. The articles "a" and "an" refer to the singular and the plural. As used herein, "CVD" is intended to include all forms of chemical vapor deposition such as MOCVD, MOVPE, OMVPE, OMCVD and RPCVD.

Unless otherwise noted, all amounts are percent by weight and all ratios are molar ratios. All numerical ranges are inclusive and combinable in any order except where it is clear that such numerical ranges are constrained to add up to 100%.

In one embodiment, the present invention relates to organometallic compounds of formula I:

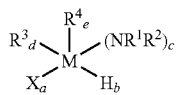

(I)

wherein M is Si or Ge; $R^1$ and $R^2$ are independently chosen from H, alkyl, alkenyl, alkynyl and aryl; each $R^3$ is independently chosen from $(C_1-C_{12})$alkyl, alkenyl, alkynyl and aryl, provided that $R^3$ is not cyclopentadienyl; each $R^4$ is independently chosen from $(C_3-C_{12})$alkyl; X is halogen; a=0-3; b=0-3; c=0-3; d=0-3; e=0-4; and a+b+c+d+e=4; wherein $R^3 \neq R^4$; wherein the sums of a+b and a+d are each $\leq 3$; provided that when M=Si the sum of b+c is $\leq 3$. In one embodiment, M=Ge. In another embodiment, c>0. In a further embodiment, c>0 and b>0. Typically, d=0-2. Particularly suitable organometallic compounds where M=Si are those wherein a=0-2, b=0-2, c=1-2, and d=0-2, and more particularly where at least two of a, b and d are not 0.

Particularly suitable organometallic compounds are the organogermanium compounds of formulae IIA and IIB:

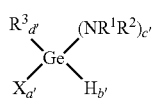

(IIA)

(IIB)

wherein $R^1$ and $R^2$ are independently chosen from alkyl, alkenyl, alkynyl or aryl; each $R^3$ is independently chosen from $(C_1-C_{12})$alkyl, alkenyl, alkynyl and aryl; each $R^4$ is independently chosen from branched and cyclic $(C_3-C_5)$ alkyl; each $R^5$ is independently chosen from $(C_1-C_{12})$alkyl, alkenyl, alkynyl and aryl; X is halogen; a'=0-3; b'=0-2; c'=1-3; d'=0-3; a'+b'+c'+d'=4; a''=0-2; b''=0-2; e''=1-2; f''=0-2; a''+b''+e''+f''=4; wherein at least two of a'', b'' and f''≠0; provided when a''=1, e''=1, f''=2, and $R^4$=$(CH_3)C$ that $R^5 \neq CH_3$; and provided that $R^3$ is branched or cyclic $(C_3-C_5)$ alkyl when c'+d'=4. In one embodiment, $R^3$ is branched or cyclic $(C_3-C_5)$alkyl. Suitable compounds of formula IIA are those wherein d'=1-3. Other suitable compounds of formula IIA are those wherein b'=1-2. Particularly suitable compounds are those wherein d'=1-3 and b'=1-2. Typically, $R^1$ and $R^2$ are independently chosen from methyl, ethyl and propyl. In another embodiment, f''=1-2. Still further, b''=1-2. Particularly suitable compounds of formula IIB are those wherein f''=1-2 and b''=1-2. $R^4$ is a bulky group and is typically tert-butyl, iso-propyl, iso-butyl, sec-butyl, neopentyl, and cyclopentyl. The bulky groups preferably are those capable of undergoing β-hydride elimination. Thus, preferred bulky groups contain a hydrogen bonded to the carbon in the beta position to the germanium.

Typical dialkylamino ($NR^1R^2$) groups include, but are not limited to, dimethylamino, diethylamino, di-iso-propylamino, ethylmethylamino, iso-propylamino, and tert-butylamino. X may be F, Cl, Br or I. Typically, X is Cl or Br. When two or more halogens are present, such halogens may be the same or different.

A wide variety of alkyl, alkenyl and alkynyl groups may be used for $R^1$, $R^2$, $R^3$ and $R^5$. Suitable alkyl groups include, without limitation, $(C_1-C_{12})$alkyl, typically $(C_1-C_6)$alkyl and more typically $(C_1-C_4)$alkyl. Exemplary alkyl groups include methyl, ethyl, n-propyl, iso-propyl, n-butyl, iso-butyl, sec-butyl, tert-butyl, pentyl, cyclopentyl, hexyl, and cyclohexyl. More typically, suitable alkyl groups include ethyl, iso-propyl, and tert-butyl. Suitable alkenyl groups include, without limitation, $(C_2-C_{12})$alkenyl, typically $(C_2-C_6)$alkenyl and more typically $(C_2-C_4)$alkenyl. Exemplary alkenyl groups include vinyl, allyl, methallyl and crotyl. Typical alkynyl groups include, without limitation, $(C_2-C_{12})$alkynyl, typically $(C_2-C_6)$alkynyl and more typically $(C_2-C_4)$alkynyl. Suitable aryl groups are $(C_6-C_{10})$aryl, including, but not limited to, phenyl, tolyl, xylyl, benzyl and phenethyl. When two or more alkyl, alkenyl or alkynyl groups are present, such groups may be the same or different.

Any of the above alkyl, alkenyl, alkynyl or aryl groups of $R^1$, $R^2$, $R^3$ and $R^5$ may optionally be substituted, such as with halogen. By "substituted" it is meant that one or more hydrogens on the alkyl, alkenyl, alkynyl or aryl group is replaced with one or more halogens.

Organometallic compounds exemplary of formula I include, but are not limited to, dichloro bis(dimethylamino) silane, chloro tris(dimethylamino) silane, dimethylamino silane, bis(dimethylamino) silane, iso-propyl (diethylamino) silane, tert-butyl silane, di-tert-butyl silane, iso-propyl silane, di-isopropyl silane, tert-butyl (methyl) silane, tert-butyl (methyl) (dichloro) silane, iso-propyl (dimethylamino) silane, iso-propyl bis(dimethylamino) silane, di-iso-propyl (dimethylamino) silane, tert-butyl (trichloro) silane, di-tert-butyl (dibromo) silane, cyclopropyl silane, cyclopropyl (dimethyl) silane, cyclopentyl (dimethylamino) silane, tert-butyl (trimethyl) germane, iso-propyl (trimethyl) germane, dimethyl germanium chloride, tert-butyl germane, iso-propyl germane, tert-butyl (trichloro) germane, iso-propyl (tribromo) germane, n-butyl germane, tri-iso-propyl germane, benzyl germane, benzyl (methyl) germane, iso-butyl germane, iso-butyl (trichloro) germane and mixtures thereof.

Exemplary organogermanium compounds of formula IIA include, without limitation, iso-propyl (dimethylamino) germane, di-iso-propyl (dimethylamino) germane, iso-propyl bis(dimethylamino) germane, iso-propyl (dimethylamino) germanium dichloride, tert-butyl (dimethylamino) germane, di-tert-butyl (dimethylamino) germane, tert-butyl bis(dimethylamino) germane, cyclopentyl (dimethylamino) germane, cyclopentyl (diethylamino) germane, methyl (dimethylamino) germane, methyl (dimethylamino) germanium dichloride, methyl (dimethylamino) germanium dibromide, methyl bis(di-iso-propylamino) germanium chloride, bis(diethylamino) germane, dichloro (diethylamino) germane, ethyl (diethylamino) germane, dichloro (ethyl) (diethylamino) germane, tert-butyl (diethylamino) germane, dichloro (tert-butyl) (diethylamino) germane, cyclopentadienyl (dimethylamino) germane, cyclopentadienyl bis(dimethylamino) germane, cyclopentadienyl (diethylamino) germane, cyclopentadienyl bis(diethylamino) germane, di-iso-propyl bis(dimethylamino) germane, dichloro bis(dimethylamino) germane, methyl bis(di-iso-propylamino) germane, di-iso-propyl bis(diethylamino) germane, bromo (dimethyl) (dimethylamino) germane, bis(dimethylamino) germane, tris(dimethylamino)germane, vinyl tris(dimethylamino) germane, divinyl (dimethylamino) germane, fluoro (divinyl) (dimethylamino) germane, benzyl (diethylamino) germane, dibenzyl (diethylamino) germane, di-iso-propyl (dimethylamino) germane, benzyl (dimethylamino) germane, and mixtures thereof.

Exemplary organogermanium compounds of formula IIB include, without limitation, tert-butyl (dichloro) germane, di-tert-butyl germane, iso-propyl (chloro) germane, di-iso-propyl (dichloro) germane, tert-butyl (methyl) germane, tert-butyl (ethyl) germane, tert-butyl (dimethyl) germane, iso-propyl (methyl) germane, di-iso-propyl (dimethyl) germane, dichloro (methyl) (iso-propyl) germane, neo-pentyl (methyl) germane, neo-pentyl (dimethyl) germane, neo-pentyl (methyl) (dichloro) germane, cyclopropyl (methyl) germane, dicyclopropyl germane, di-iso-propyl germane, cyclopropyl (methyl) (dichloro) germane, dibromo (methyl) (tert-butyl) germane, cyclopentyl (dichloro) (methyl) germane, cyclopentyl (dichloro) germane, cyclopentyl (ethyl) (dibromo) germane, diethyl (tert-butyl) (fluoro) germane, and mixtures thereof.

The above-described organometallic compounds are particularly suitable for use as precursors for CVD of films containing silicon, germanium and combinations thereof.

The present organometallic compounds may be prepared by a variety of procedures. Typically, the organometallic compounds of the present invention are prepared starting from a compound of the formula $MY_4$ where M is silicon or germanium and Y is a reactive group such as a halogen, an acetate or a $(C_1-C_4)$alkoxy, with halogens being most typical. As used herein, a reactive group is any group attached to the metal that is displaced or exchanged in a subsequent reaction. The preparation of the present organometallic compounds will be described with respect to germanium precursors for purposes of illustration, however, such preparation is equally applicable to silicon, as well as other Group IV elements.

Dialkylamino-substituted organometallic compounds of the present invention may be prepared by the reaction of a dialkylamine in liquid or gaseous forms with a metal compound having one or more reactive groups and more typically is prepared by the reaction of a dialkylamino lithium reagent with such metal having one or more reactive groups. Such reactions are typically performed in a hydrocarbon solvent, such as but not limited to hexane, heptane, octane, nonane, decane, dodecane, toluene, and xylene. Preferably, such solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen. For example, germanium tetrachloride may be reacted with a sufficient amount of dialkylamino lithium reagent to provide a desired dialkylamino germanium halide compound. This reaction is illustrated in Equation 1.

$$2LiNMe_2 + GeCl_4 \rightarrow (NMe_2)_2GeCl_2 + 2LiCl \quad (1)$$

Alkyl, alkenyl, alkynyl and aryl substituted organometallic compounds may be prepared using Grignard or organolithium reactions. Such reactions are well known to those skilled in the art. In a typical Grignard reaction, a compound having one or more reactive groups is reacted with a Grignard reagent, such as methyl magnesium bromide or allyl magnesium bromide in an ethereal solvent. Typical ethereal solvents include, without limitation, diethyl ether, di-isopropyl ether, n-butyl ether, iso-pentyl ether, dihexyl ether, diheptyl ether, tetrahydrofuran, dioxane, monoglyme, diglyme, diethylene glycol dibutyl ether, diethylene glycol monobutyl ether, ethylene glycol dibutyl ether, ethylene glycol monohexyl ether, ethylene glycol monobenzyl ether, tetraethylene glycol dimethyl ether, triethylene glycol dimethyl ether, butyl phenyl ether, and dicyclohexyl ether. Such solvents are typically deoxygenated prior to use as described above. This reaction is illustrated in Equation 2.

$$(NMe_2)_2GeCl_2 + AllylMgBr \rightarrow (NMe_2)_2Ge(Allyl)Cl + MgBrCl \quad (2)$$

In a typical organolithium reaction, a compound having one or more reactive groups is reacted with an organolithium reagent, such as methyl lithium, tert-butyl lithium, n-butyl lithium and phenyl lithium in a suitable hydrocarbon or ethereal solvent. Suitable solvents are those described above for the dialkylamino lithium reaction. Equation 3 illustrates the reaction of bis(dimethylamino)-germanium dichloride with iso-propyl lithium.

$$(NMe_2)_2GeCl_2 + i\text{-}PrLi \rightarrow (NMe_2)_2Ge(i\text{-}Pr)Cl + LiCl \quad (3)$$

In another embodiment, a compound having two or more reactive groups may be reacted with two different lithium reagents in one pot. Such different lithium reagents may be two different organolithium reagents, two different dialkylamino lithium reagents or a mixture of an organolithium reagent and a dialkylamino lithium reagent. In such reaction, the different lithium reagents may be added to the reaction simultaneously or in a stepwise manner. Equation 4 illustrates this reaction sequence for the reaction of germanium tetrachloride with tert-butyl lithium and dimethylamino lithium.

$$t\text{-}BuLi + GeCl_4 + LiNMe_2 \rightarrow (NMe_2)(tBu)GeCl_2 + 2\ LiCl \quad (4)$$

In a further embodiment, the alkyl-, alkenyl-, alkynyl- and aryl-substituted germanes may be prepared by a transalkylation reaction using the appropriately substituted aluminum compound. For example, methyl-substituted germanes may be prepared by the reaction of an appropriate amount of trimethylaluminum with an appropriate amount of germanium tetrachloride in the presence of a tertiary amine. Such amounts are well within the ability of those skilled in the art. Equation 5 illustrates this reaction sequence for the reaction of germanium tetrachloride with trimethylaluminum.

$$GeCl_4 + AlMe_3 \rightarrow Me_3GeCl + AlCl_3 \quad (5)$$

Such transalkylation reactions using alkyl aluminum compounds are preferably performed in the presence of a tertiary amine. Any tertiary amine may suitably be used. Exemplary tertiary amines include, but are not limited to, those having the general formula NR'R''R''', wherein R'', R'' and R''' are independently selected from $(C_1\text{-}C_6)$alkyl, di$(C_1\text{-}C_6)$alkylamino-substituted $(C_1\text{-}C_6)$alkyl, and phenyl and wherein R' and R'' may be taken together along with the nitrogen to which they are attached to form a 5-7 membered heterocyclic ring. Such heterocyclic ring may be aromatic or non-aromatic. Particularly suitable tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N',N'-tetramethyl-1,2-diaminoethane, pyridine, pyrazine, pyrimidine, and mixtures thereof. Preferred amines include trimethylamine, triethylamine, tri-n-propylamine, tri-iso-propylamine, and tri-n-butylamine. More preferably, the tertiary amine is triethylamine or tri-n-propylamine. It will be appreciated by those skilled in the art that more than one tertiary amine may be used in the present invention. Such tertiary amines are generally commercially available from a variety of sources. Such tertiary amines may be used as is or, preferably further purified prior to use.

Germanes containing one or more Ge—H bonds can be prepared by the reduction of a germanium halide. In general, such reduction is performed in a dried organic solvent which has been deoxygenated as described above. A wide variety of organic solvents are suitable. A wide variety of reducing agents may be used in the present invention. Particularly useful reducing agents include reactive metals; hydrides such as sodium hydride and lithium hydride; borohydride reducing agents such as sodium borohydride and lithium borohydride; aluminum hydride reducing agents such as lithium aluminum hydride and $NaAlH_2(OCH_2CH_2OCH_3)_2$; borane reducing agents such as dimethylamine borane, cyclohexylamine borane, morpholine borane, and the like. In another embodiment, such reduction step may be performed in the presence of a tertiary amine. In such reaction, the tertiary amine, organic solvent and reducing agent may be combined in any order prior to reacting with the germanium halide. Suitable temperatures for forming the germanes of the present invention are from below ambient temperature to 90° C. This reduction reaction is illustrated in Equations 6 and 7.

$$(NMe_2)_2Ge(Allyl)Cl + LiAlH_4 \rightarrow (NMe_2)_2Ge(Allyl)H \quad (6)$$

$$(NMe_2)(tBu)GeCl_2 + LiAlH_4 \rightarrow (NMe_2)(tBu)GeH_2 \quad (7)$$

In each of the above described reactions, the mole ratio of reagent to the metal compound depends upon the number of reactive groups in the metal compound that are to be exchanged. Typically, the mole ratio of any of the above reagents to the reactive group is from 1:1 to 1.3:1. Accordingly, if two reactive groups in the metal compound are to be exchanged, the mole ratio of reagent to metal compound is from 2:1 to 2.6:1, which corresponds to a mole ratio of reagent to reactive group of 1:1 to 1.3:1. Other amounts and ratios may be used depending upon the specific reaction conditions employed.

It will be appreciated by those skilled in the art that the order of the above reactions may be performed in any order.

Typically, any step of reducing a metal-halide compound to form a metal-hydrogen compound will be performed last, although other orders of reaction may be advantageous.

Any of the above described methods of preparing the desired organometallic precursor compounds may be performed in a batch, semi-batch, continuous or semi-continuous mode. For example, the present invention provides a batch as well as semi-continuous process for the preparation of organometallic compounds of Group IV, including the steps of delivering a Group IV metal compound and alkylating agent independently to a reaction zone maintained at a predetermined temperature sufficient to allow the alkylation to proceed and the product is then separated once the reaction is complete. The organometallic product is collected at the outlet preferably located at the top of the reactor while the byproduct in non-vaporized state is removed as waste from the reactor at the end of the reaction. The addition of reagents in a multi-step alkylation may be either in a simultaneous or sequential manner. The rate of addition of the various reagents may be controlled by using appropriate flow controllers that are known in the art.

In another embodiment, the present invention also provides a continuous process for the preparation of organometallic compounds of Group IV, including the steps of delivering a Group IV metal compound and alkylating agent independently to a reaction zone maintained at predetermined temperature sufficient to allow the alkylation to proceed and the product to vaporize. The organometallic product is then collected at the outlet preferably located at the top of the reactor while the byproduct in non-vaporized state is removed as waste from the base of the reaction zone. The continuous operation to deliver organometallic compound may be controlled by continuous transfers of the reagents to the reaction zone, their delivery rates, the vapor-liquid equilibrium established between the vapor of the product moving upward and the liquid byproduct moving downward, the take-off rate of the product at the outlet of the reaction zone, and the rate of removal of the byproduct waste from the base of the reaction zone.

In a further embodiment, the present invention also provides a continuous process for the preparation of organometallic hydrides of Group IV, including the steps of delivering a Group IV metal halide and reducing agent independently to a reaction zone maintained at predetermined temperature sufficient to allow the reduction to proceed and the product to evaporate. The organometallic product is then collected at the outlet preferably located at the top of the reactor while the byproduct in non-vaporized state is removed as waste from the base of the reaction zone. The continuous operation to deliver organometallic compound may be controlled by the continuous transfers of the reagents to the reaction zone, their delivery rates, the vapor-liquid equilibrium established between the vapor of the product moving upward and the liquid byproduct moving downward, the take-off rate of the product at the top outlet of the reaction zone, and the rate of removal of the byproduct waste from the base of the reaction zone.

An advantage of the present invention is that the present organometallic compounds are substantially free of metallic impurities such as zinc and aluminum, and preferably free of zinc and aluminum. In particular, the present organogermanium compounds are substantially free of zinc, aluminum and silicon, and preferably free of such impurities. By "substantially free" it is meant that the compounds contain less than 0.5 ppm of such impurities, and preferably less than 0.25 ppm. In another embodiment, the present organometallic compounds have "5-nines" purity, i.e. a purity of $\geq 99.999\%$.

More typically, the present compounds have a purity of "6-nines", i.e. $\geq 99.9999\%$. Certain of these compounds are typically liquids at room temperature and provide safer alternatives than conventional silicon and germanium precursors for vapor phase deposition.

The present organometallic compounds are particularly suitable for use as precursors in all vapor deposition methods such as LPE, MBE, CBE, ALD and CVD, and particularly MOCVD and metalorganic vapor phase epitaxy ("MOVPE"). More particularly, the present organometallic compounds are suitable for use as precursors in the vapor phase deposition of silicon-germanium ("SiGe") films. Such films are useful in the manufacture of electronic devices, such as integrated circuits, and optoelectronic devices, and particularly in the manufacture of heterojunction bipolar transistors.

Films of silicon, germanium, and combinations thereof are typically deposited by first placing the desired organometallic precursor compound, i.e. source compound, in a delivery device, such as a cylinder, having an outlet connected to a deposition chamber. A wide variety of cylinders may be used, depending upon the particular deposition apparatus used. When the precursor compound is a solid, the cylinders disclosed in U.S. Pat. No. 6,444,038 (Rangarajan et al.) and U.S. Pat. No. 6,607,785 (Timmons et al.), as well as other designs, may be used. For liquid precursor compounds, the cylinders disclosed in U.S. Pat. No. 4,506,815 (Melas et al) and U.S. Pat. No. 5,755,885 (Mikoshiba et al) may be used, as well as other liquid precursor cylinders. The source compound is maintained in the cylinder as a liquid or solid. Solid source compounds are typically vaporized or sublimed prior to transportation to the deposition chamber.

Accordingly, the present invention provides a device for feeding a fluid stream saturated with an organometallic compound suitable for depositing a metal film containing silicon, germanium, and combinations thereof to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing one or more organometallic compounds of formula I

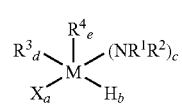
(I)

wherein M is Si or Ge; $R^1$ and $R^2$ are independently chosen from H, alkyl, alkenyl, alkynyl and aryl; each $R^3$ is independently chosen from $(C_1-C_{12})$alkyl, alkenyl, alkynyl and aryl, provided that $R^3$ is not cyclopentadienyl; each $R^4$ is independently chosen from $(C_3-C_{12})$alkyl; X is halogen; a=0-3; b=0-3; c=0-3; d=0-2; e=0-4; and a+b+c+d+e=4; wherein $R^3 \neq R^4$; wherein the sums of a+b and a+d are each $\leq 3$; provided that when M=Si the sum of b+c is $\leq 3$; the inlet opening being in fluid communication with the chamber and the chamber being in fluid communication with the outlet opening.

In a still further embodiment, the present invention provides an apparatus for chemical vapor deposition of metal films including one or more devices for feeding a fluid stream saturated with one or more organometallic compounds described above.

The source compound is typically transported to the deposition chamber by passing a carrier gas through the cylinder.

Suitable carrier gasses include nitrogen, hydrogen, and mixtures thereof. In general, the carrier gas is introduced below the surface of the source compound, and passes up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The deposition chamber temperature is from 200° to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates may contain one or more additional layers of materials, such as, but not limited to, dielectric layers and conductive layers such as metals. Such substrates are particularly useful in the manufacture of electronic devices, such as integrated circuits.

Deposition is continued for as long as desired to produce a film having the desired properties. Typically, the film thickness will be from several hundred angstroms to several tens of nanometers to several hundreds of microns or more when deposition is stopped.

Thus, the present invention provides a method for depositing a metal-containing film a substrate including the steps of: a) conveying one or more organometallic source compounds of formula I in the gaseous phase to a deposition chamber containing the substrate; b) decomposing the one or more organometallic source compounds in the deposition chamber; and c) depositing the metal-containing film the substrate, wherein the metal-containing film includes silicon, germanium and combinations thereof. The organogermanium compounds of formulae IIA and IIB may be suitably used in such method.

The present invention further provides a method for manufacturing an electronic device including the step of depositing a film containing silicon, germanium, and combinations thereof on an electronic device substrate including the steps of: a) conveying one or more organometallic source compounds of formula I in the gaseous phase to a deposition chamber containing the substrate; b) decomposing the one or more organometallic source compounds in the deposition chamber; and c) depositing a film containing silicon, germanium and combinations thereof on the substrate. In an alternate embodiment, organogermanium compounds of formulae IIA and IIB may be used in such method.

The present invention is particularly suitable for the deposition of silicon-containing films, germanium-containing films and SiGe films. SiGe films are being employed for two technologies. One well-established major application is Bipolar CMOS or BiCMOS where a thin (40 to 80 nm) SiGe film is used as the base of a high frequency HBT. The substrate for the deposition of this SiGe base film and the subsequent Si collector film is a highly structured silicon wafer with the CMOS circuitry mostly finished. The other application for SiGe CVD is the area of strained silicon or s-Si. Here a deposition of a thick 3 to 5 micrometer SiGe layer takes place on a plain silicon wafer. Subsequent to the growth of the SiGe film a thin (20 nm) Si film is grown. This silicon film adopts the crystal lattice of the underlying SiGe layer (strained silicon). Strained silicon shows much faster electrical responses than regular silicon.

In another embodiment, a method for fabricating a device containing a group of silicon-germanium layers is illustrated by the steps of: i) providing a substrate including a surface layer of a group IV element, ii) maintaining the substrate at a temperature ranging from 400° C. to 600° C., iii) forming a layer of $Si_{1-x}Ge_x$, where x ranges from 0 to 0.50, on the substrate by MOCVD using any of the above-described silicon and germanium precursors; iv) maintaining the substrate at about the temperature of step i) and continuing the silicon precursor flow with the germanium precursor flow completely switched off, in order to obtain abrupt interfaces, and v) maintaining the substrate at about the temperature of step i), and forming a cap layer of strained silicon, thereby improving the mobility of electrons and speed of the device.

The following examples are expected to further illustrate various aspects of the present invention, but are not intended to limit the scope of the invention in any aspect. All manipulations are performed in an inert atmosphere, typically under an atmosphere of dry nitrogen.

Example 1

Dimethylamino germanium trichloride is expected to be synthesized according to the equation:

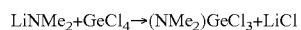

$$LiNMe_2 + GeCl_4 \rightarrow (NMe_2)GeCl_3 + LiCl$$

To a stirred solution of germanium tetrachloride (50 g, 0.233 moles) in pentane (100 mL) maintained at 0° C., is added dropwise a solution of lithium dimethylamide in diethyl ether (11.898 g, 0.233 moles, 50 mL) via pressure equalized addition funnel. The addition lasts for approximately 30 minutes. When the addition is completed, the resulting mixture is allowed to slowly warm to room temperature after which a suspension is expected to be obtained.

When the suspension settles, the supernatant mother liquor is separated using a siphon technique. The precipitate of lithium chloride byproduct is washed with fresh pentane and the washings are separated via siphon under nitrogen atmosphere, and are subsequently combined with the mother liquor. The pentane/ether solvents are then removed via atmospheric pressure distillation by heating the reaction mass to 60° C. The expected crude product obtained may be further purified by vacuum distillation and is expected to yield high purity dialkylamino germanium trichloride free of metallic impurities and organic solvents.

Example 2

The procedure of Example 1 is repeated except that silicon tetrachloride is used instead of germanium tetrachloride and is expected to prepare dialkylamino silicon trichloride. The product is expected to have total metallic impurities of <5 ppm.

Example 3

Ethyl germanium trichloride is expected to be synthesized according to the equation:

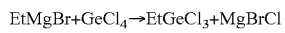

$$EtMgBr + GeCl_4 \rightarrow EtGeCl_3 + MgBrCl$$

To a stirred solution of germanium tetrachloride (50 g, 0.233 moles) in diethylether (100 mL) maintained at 0° C., is added dropwise a solution of ethylmagnesium bromide in diethyl ether (0.233 moles, 78 mL of 3.0 M) via pressure equalized addition funnel. This addition lasts for approximately 45 minutes. When the addition is completed, the resulting mixture is allowed to slowly warm to room temperature after which a suspension is expected to be obtained.

When the suspension settles, the supernatant mother liquor is separated using a siphon technique. The expected precipitate of magnesium halide byproduct is washed with fresh diethylether and the washings are separated via siphon under nitrogen atmosphere, and are subsequently combined with the mother liquor. The ether solvent is then removed via atmospheric pressure distillation to leave the expected crude product. The reaction mixture is then heated to 50 to 60° C. using an oil bath. The crude product may be further purified via fractional distillation and is expected to yield high purity ethyl germanium trichloride free of metallic impurities and organic solvents.

Example 4

The procedure of Example 3 is repeated except that silicon tetrachloride is used instead of germanium tetrachloride and is expected to provide ethyl silicon trichloride.

Example 5

Ethyl germanium trichloride is expected to be synthesized according to the equation:

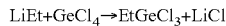

$$LiEt + GeCl_4 \rightarrow EtGeCl_3 + LiCl$$

To a cool stirred solution of germanium tetrachloride (50 g, 0.233 moles) in benzene (100 mL) maintained at 0° C., is added dropwise a solution of ethyllithium in benzene/cyclohexane (90:10) (0.25 moles, 500 mL of 0.5 M) via pressure equalized addition funnel. This addition lasts for approximately 60 minutes. When the addition is complete, the resulting mixture is allowed to slowly warm to room temperature after which a suspension is expected. When the suspension settles, the supernatant mother liquor is separated using a siphon technique. The expected precipitate of lithium halide byproduct is washed with fresh cyclohexane and the washings are separated via siphon under nitrogen atmosphere, and are then subsequently combined with the mother liquor. The solvent mixture is then removed via atmospheric pressure distillation to leave the expected crude product. The reaction mixture is then heated to 50° to 60° C. using an oil bath. The expected crude product may be further purified via its fractional distillation and is expected to yield high purity ethyl germanium trichloride free of metallic impurities and organic solvents.

Example 6

The procedure of Example 5 is repeated except that silicon tetrachloride is used instead of germanium tetrachloride and is expected to provide ethyl silicon trichloride.

Example 7

Ethyl germane is expected to be synthesized according to the equation:

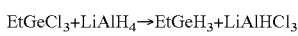

$$EtGeCl_3 + LiAlH_4 \rightarrow EtGeH_3 + LiAlHCl_3$$

To a room temperature stirred suspension of excess reducing agent (either $LiAlH_4$ or $NaBH_4$, 0.5 moles) in n-butyl ether is added dropwise $EtGeCl_3$ obtained from Example 5 (50 g, 0.240 moles) dissolved in n-butyl ether (100 mL) via pressure equalized dropping funnel under nitrogen. An expected exothermic reaction occurs yielding a gray suspension. Crude product is distilled pot to pot under vacuum along with some n-butyl ether solvent. The expected final product is then isolated from n-butyl ether via fractional distillation.

Example 8

Bis(dimethylamino) germane is expected to be synthesized according to the equation:

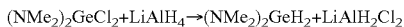

$$(NMe_2)_2GeCl_2 + LiAlH_4 \rightarrow (NMe_2)_2GeH_2 + LiAlH_2Cl_2$$

To a room temperature stirred suspension of excess reducing agent (0.5 moles, either $LiAlH_4$ or $NaBH_4$) in n-butyl ether is added dropwise $(NMe_2)_2GeCl_2$ (0.2241 moles) dissolved in n-butyl ether via pressure equalized dropping funnel under nitrogen. An exothermic reaction is expected yielding a gray-white suspension. The expected crude product is distilled pot to pot under vacuum along with some n-butyl ether solvent. The expected final product may be isolated from n-butyl ether via fractional distillation.

Example 9

The procedure of Example 8 is repeated except that bis(dimethylamino)silicon dichloride is used instead of bis(dimethylamino) germanium dichloride and is expected to provide bis(dimethylamino)silane.

Example 10

Dimethylamino ethyl germanium dichloride is expected to be synthesized according to the equation:

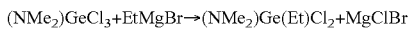

$$(NMe_2)GeCl_3 + EtMgBr \rightarrow (NMe_2)Ge(Et)Cl_2 + MgClBr$$

To a low temperature stirred solution of $(NMe_2)GeCl_3$ (50 g, 0.2241 moles) in diethyl ether (100 mL) is added dropwise EtMgBr in diethyl ether (0.23 moles) via pressure equalized dropping funnel under nitrogen. An exothermic reaction is expected yielding a suspension. The expected crude product is distilled from the mixture under full vacuum to yield product mixed with diethyl ether. The expected final product is obtained via fractional distillation at atmospheric pressure after removal of bulk diethyl ether solvent. The expected product may then further purified by one more fractional distillation.

Example 11

The procedure of Example 10 is repeated except that dimethylamino silicon trichloride is used and is expected to provide dimethylamino ethyl silicon dichloride.

Example 12

Dimethylamino ethyl germane is expected to be synthesized according to the equation:

$(NMe_2)Ge(Et)Cl_2 + LiAlH_4 \rightarrow (NMe_2)Ge(Et)H_2 + LiAlH_2Cl_2$ To a room temperature stirred suspension of excess reducing agent (0.5 moles, either LiAlH$_4$ or NaBH$_4$) in n-butyl ether is added dropwise $(NMe_2)(Et)GeCl_2$ from Example 10 (50 g, 0.23 moles) dissolved in n-butyl ether via pressure equalized dropping funnel under nitrogen. An exothermic reaction is expected yielding a gray suspension. The expected crude product is then distilled pot to pot under vacuum along with some n-butyl ether solvent. The expected final product may be isolated from n-butyl ether via fractional distillation.

Example 13

The compounds in the following Table are expected to be prepared according to one or more of the previous Examples. The abbreviations, "Et", "Me" and "i-Pr" refer to "ethyl", "methyl" and "iso-propyl", respectively. The abbreviation "Ph" refers to a phenyl group.

| Germanium Precursors | Silicon Precursors |
|---|---|
| $(NMe_2)GeH_3$ | $(NEt_2)(Me)SiH_2$ |
| $(NMe_2)_2GeH_2$ | $(Ni\!-\!Pr_2)_2SiCl_2$ |
| $(NMe_2)_3GeH$ | $(i\text{-}Pr)_3SiCl$ |
| $(CH_2\!=\!CH\!-\!CH_2)GeH_3$ | $(CH_2\!=\!CH\!-\!CH_2)SiH_3$ |
| $(CH_2\!=\!CH\!-\!CH_2)_2GeH_2$ | $(CH_2\!=\!CH\!-\!CH_2)_2SiH_2$ |
| $(CH_2\!=\!CH\!-\!CH_2)_3GeH$ | $(CH_2\!=\!CH\!-\!CH_2)_3SiH$ |
| $(CH_2\!=\!CH)GeH_3$ | $(CH_2\!=\!CH)SiH_3$ |
| $(CH_2\!=\!CH)_2GeH_2$ | $(CH_2\!=\!CH)_2(Me_3C)SiH$ |
| $(CH_2\!=\!CH)_3GeH$ | $(CH_2\!=\!CH)_3SiH$ |
| $(CH_2\!=\!CH)Ge(NMe_2)_3$ | $(CH_2\!=\!CH)Si(NMe_2)_3$ |
| $(CH_2\!=\!CH)_2Ge(NMe_2)_2$ | $(CH_2\!=\!CH)_2Si(NMe_2)_2$ |
| $(CH_2\!=\!CH)_3Ge(NMe_2)$ | $(CH_2\!=\!CH)_3Si(NMe_2)$ |
| $(Ph\text{-}CH_2)GeH_3$ | $(Ph\text{-}CH_2)SiH_3$ |
| $(Ph\text{-}CH_2)_2GeH_2$ | $(Ph\text{-}CH_2)_2(Me)SiH$ |
| $(Ph\text{-}CH_2)_3GeH$ | $(Ph\text{-}CH_2)_3(NMe_2)Si$ |
| $(Me_3C)GeH_3$ | $(Me_3C)SiH_3$ |
| $(Me_3C)_2GeH_2$ | $(Me_3C)_2SiH_2$ |
| $(Me_3C)_3GeH$ | $(Me_3C)_3SiCl$ |
| $(Me_3C)(NMe_2)GeH_2$ | $(Me_3C)(NMe_2)SiH_2$ |
| $(Me_2N)(i\text{-}Pr)GeH_2$ | $i\text{-}PrSiH_3$ |
| $(Me)(Me_3C)GeH_2$ | $(Et)(Me_3C)SiH_2$ |
| $(i\text{-}Pr)_2GeH_2$ | $(Me_2N)_2SiMe_2$ |
| $(Me)_2(Me_3C)GeH$ | $(Me_2N\!-\!C_2H_4)_2SiH_2$ |
| $(Me)(NMe_2)GeH_2$ | $(Me_2N\!-\!C_3H_6)(NMe_2)SiH_2$ |
| $(NMe_2)(Et)GeH_2$ | $(Me_2N\!-\!C_3H_6)(NMe_2)(Et)SiH$ |
| $(NMe_2)_2(Et)GeCl$ | $(Me_2N\!-\!C_3H_6)(NMe_2)(Et)SiCl$ |
| $(Me_3C)(NMe_2)GeCl_2$ | $(Me_3C)(NMe_2)SiCl_2$ |
| $(i\text{-}Pr)_2(NMe_2)GeCl$ | $(i\text{-}Pr)_2(NMe_2)SiCl$ |

Example 14

Tert-buylmethylgermane was synthesized according to the following equation.

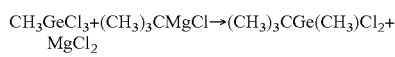
$CH_3GeCl_3 + (CH_3)_3CMgCl \rightarrow (CH_3)_3CGe(CH_3)Cl_2 + MgCl_2$

$(CH_3)_3CGe(CH_3)Cl_2 + LiAlH_4 \rightarrow (CH_3)_3CGe(CH_3)H_2 + LiAlH_2Cl_2$ To a stirred solution of methylgermanium trichloride (52 g, 0.24 mol) in ethyldiglyme (100 mL) maintained at below 40° C. was added dropwise a solution of tert-butylmagnesium chloride in butyl diglyme (0.275 mol, 250 mL) via pressure equalized addition funnel. The addition lasted for 180 minutes. When the addition was completed, the reaction mixture was added to a stirred mixture of lithium hydride (12 g) in ethyldiglyme (200 mL) using a transfer line in a dropwise manner. The crude product (16 g) was obtained by vacuum distillation at 32 mtorr and was confirmed by NMR to be the desired germane contaminated with solvent (NMR spectrum contained a quadruplet at 3.82 ppm, a singlet at 1.00 ppm and a triplet at 0.14 ppm, corresponding to GeH$_2$, (CH$_3$)$_3$C and CH$_3$, respectively).

Example 15

Trimethylpropylgermane was synthesized according to the following equation.

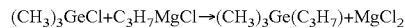
$(CH_3)_3GeCl + C_3H_7MgCl \rightarrow (CH_3)_3Ge(C_3H_7) + MgCl_2$

To a stirred solution of trimethylgermanium chloride (120 g, 0.78 mol) in butyldiglyme (200 mL) maintained at below 40° C. was added dropwise a solution of n-propylmagnesium chloride in diethylether (0.780 mol, 390 mL) via pressure equalized addition funnel. The addition lasted for 120 minutes. When the addition was completed, the reaction mixture was heated to gentle reflux for two hours. The crude product was obtained by vacuum distillation and was confirmed by NMR to be the desired germane. The crude product was further purified via its fractional distillation (80 g, Yield=70%).

Example 16

Trimethylisopropylgermane was synthesized according to the following equation.

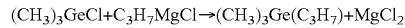
$(CH_3)_3GeCl + C_3H_7MgCl \rightarrow (CH_3)_3Ge(C_3H_7) + MgCl_2$

To a stirred solution of excess $^i$PrMgCl in butyl diglyme (750 mL, 1.05 moles) was added at room temperature neat Me$_3$GeCl (130 g, 0.848 moles) in a controlled manner via 16 gauge stainless steel cannula. The addition took 3 hours during which time the temperature rose to ca. 50° C. After the addition was completed and the mixture was allowed to cool to room temperature, crude product was isolated by full vacuum transfer with heating of the pot gradually to 85° C., into a dry ice cooled receiver. The crude product was atmospherically distilled using a 1.5 ft vacuum jacketed packed column to yield a main fraction distilling between 93-97° C. (105 g, Yield=77%). H nmr spectrum contained a doublet at 1.0 ppm, a multiplet at 0.94 ppm, and a singlet at 0.06 ppm corresponding to CH$_3$, CH and GeCH$_3$ respectively.

Example 17

Dimethylaminopropyltrimethylgermane was synthesized according to the following equation.

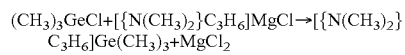
$(CH_3)_3GeCl + [\{N(CH_3)_2\}C_3H_6]MgCl \rightarrow [\{N(CH_3)_2\}C_3H_6]Ge(CH_3)_3 + MgCl_2$ To a stirred solution of excess dimethylaminopropylmagnesium chloride in tetrahydrofuran (0.38 moles) was added at room temperature neat Me$_3$GeCl (52 g, 0.34 moles) in a controlled manner. The addition took 1 hour during which time the temperature rose to ca. 44° C. After the addition was completed and the mixture was heated to 75° C. for 1 hour. The reaction mixture was then allowed to cool to room temperature, and de-ionized water (150 mL) was added to the reaction mass in controlled manner. The organic layer containing crude product was isolated by siphoning. The aqueous layer was extracted with diethylether (100 mL), and the extracted solution was combined with the product. The organic layers were dried over molecular sieves (5 Å) over 16 hours. The solvents (tetrahydrofuran and diethylether) were removed by atmospheric pressure distillation, while the crude product (45 g) was obtained by vacuum distillation. $^1$H nmr spectrum confirmed the product to be the desired dialkylaminopropyltrimethylgermanium.

Example 18

Tertiary-butyl germanium trichloride was synthesized according to the equation:

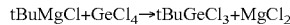

tBuMgCl+GeCl$_4$→tBuGeCl$_3$+MgCl$_2$

To a cool stirred solution of germanium tetrachloride (95 g, 0.443 moles) in butyl diglyme (150 mL) maintained at 0° C., was added dropwise a solution of t-butyl magnesium chloride in butyl diglyme (0.422 moles, 410 mL of 1.03 M) via pressure equalized addition funnel. A slight excess of germanium tetrachloride was maintained. This addition lasted for 120 minutes. When the addition was complete, the resulting mixture was allowed to slowly warm to room temperature after which a suspension of magnesium chloride was observed. The product, t-butyl germanium trichloride was isolated by vacuum distillation from the magnesium chloride and butyl diglyme. The vacuum was slowly lowered to full vacuum and the temperature was raised to 50° C. to obtain the final product. The crude product was found to be contaminated with trace butyl diglyme as verified by FTNMR. The crude product was further purified by a second vacuum distillation.

Example 19

Tertiary-butyl germanium trichloride was synthesized according to the equation:

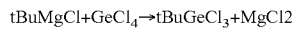

tBuMgCl+GeCl$_4$→tBuGeCl$_3$+MgCl2

To a cool stirred solution of germanium tetrachloride (100 g, 0.443 moles) in linear alkyl benzene (200 mL) maintained at 0° C., was added dropwise a solution of t-butyl magnesium chloride in diethyl ether (0.466 moles, 233 mL of 2.0 M) via pressure equalized addition funnel. A slight excess of germanium tetrachloride was maintained. This addition lasted for 120 minutes. When the addition was complete, the resulting mixture was allowed to slowly warm to room temperature after which a suspension of magnesium chloride was observed. The product, t-butyl germanium trichloride, and diethyl ether were removed from the reaction mixture by vacuum distillation. The resultant material was then subjected to atmospheric distillation to remove the ether. After the removal of ether, pure product was obtained by the purification of crude product by vacuum sublimation (40 g, Yield=37%).

Example 20

A group of Si$_x$Ge$_{1-x}$ epitaxial structures are expected to be grown by MOCVD on (001) sapphire substrates. MOCVD is performed using bis(dimethylamino)silane and bis(dimethylamino)-germane as precursors, and H$_2$ and/or N$_2$ as the carrier gases. For this group of layers, a 1 to 2 μm thick Si$_{0.9}$Ge$_{0.1}$ layer is first expected to be grown on a silicon substrate. Subsequent layers of composition Si$_{0.8}$Ge$_{0.2}$, Si$_{0.7}$Ge$_{0.3}$, and Si$_{0.6}$Ge$_{0.4}$ are expected to be grown by increasing the mass flow rate of the germanium precursor. The growth temperature is maintained between 350° C. and 450° C. After deposition of the Si$_{1-x}$Ge$_x$ graded layers, the silicon precursor flow is continued with the germanium precursor flow completely switched off, in order to obtain abrupt interfaces. Silicon deposition is thus carried out using the graded SiGe as the underlying layer, and epitaxial strained silicon layer is expected to be deposited as the cap layer.

| Germanium Precursors | Silicon Precursors |
|---|---|
| Di-tert-butyl germane | Di-tert-butyl silane |
| Mono-tert-butyl germane | Mono-tert-butyl silane |
| Tri-tert-butyl germane | Tri-tert-butyl silane |
| Mono(dimethylamino) germane | Mono(dimethylamino) silane |
| Bis(dimethylamino) germane | Bis(dimethylamino) silane |
| Tris(dimethylamino) germane | Tris(dimethylamino) silane |
| Mono-tert-butyl germane | Mono(dimethylamino) silane |
| Tert-Butyl(dimethylamino) germane | Di-tert-butyl silane |
| Iso-Propyl bis(dimethylamino)germane | Bis(diethylamino)silane |
| Di-tert-butyl germane | Mono-tert-butyl silane |
| Methyl tert-butyl germane | Mono-tert-butyl silane |
| Mono-iso-butyl germane | Dichlorosilane |
| Trichloro iso-butyl germane | Disilane |
| Trichloro tert-butyl germane | Tetrachlorosilane |
| Trichloro ethyl germane | Dimethyl dichlorosilane |

What is claimed is:

1. A compound of formula IIA or IIB:

wherein R$^1$ and R$^2$ are independently chosen from alkyl, alkenyl, alkynyl or aryl; each R$^3$ is independently chosen from (C$_1$-C$_{12}$)alkyl, alkenyl, alkynyl and aryl; each R$^4$ is independently chosen from branched and cyclic (C$_3$-C$_5$) alkyl; each R$^5$ is independently chosen from (C$_1$-C$_{12}$)alkyl, alkenyl, alkynyl and aryl; X is halogen; a'=0-3; b'=1-2; c'=1-3; d'=0-3; a'+b'+c'+d'=4; a"=0-2; b"=1-2; e"=1-2; f"=0-2; a"+b"+e"+f"=4; wherein at least two of a", b" and f"≠0.

2. The compound of claim 1 wherein R$^3$ is branched or cyclic (C$_3$-C$_5$)alkyl.

3. The compound of claim 1 wherein f"=1-2.

4. The compound of claim 1 wherein d'=1-3.

5. The compound of claim 1 wherein R$^4$ is chosen from tert-butyl, iso-propyl, iso-butyl, sec-butyl neopentyl and cyclopentyl.

* * * * *